US005279282A

United States Patent [19]

Oppelt

[11] Patent Number: 5,279,282

[45] Date of Patent: Jan. 18, 1994

[54] ACOUSTIC WAVE GENERATOR HAVING A CIRCULATABLE, LIQUID ACOUSTIC PROPAGATION MEDIUM

[75] Inventor: Sylvester Oppelt, Memmelsdorf, Fed. Rep. of Germany

[73] Assignee: Siemens Aktiengesellschaft, Munich, Fed. Rep. of Germany

[21] Appl. No.: 932,673

[22] Filed: Aug. 20, 1992

[30] Foreign Application Priority Data

Sep. 27, 1991 [DE] Fed. Rep. of Germany ....... 4132343

[51] Int. Cl.[5] .............................................. A61B 17/22

[52] U.S. Cl. .......................... 128/24 AA; 128/24 EL; 367/166; 367/171

[58] Field of Search .................. 128/24; 181/118, 120; 367/147, 166, 171, 150, 157, 163, 174, 175

[56] References Cited

U.S. PATENT DOCUMENTS

| | | | |
|---|---|---|---|
| 4,530,358 | 7/1985 | Forssmann et al. | 128/24 EL |
| 4,630,607 | 12/1986 | Duinker et al. | 128/24 EL |
| 4,715,375 | 12/1987 | Nowacki et al. | 128/24 EL |
| 4,798,196 | 1/1989 | Nowacki et al. | 128/24 EL |
| 5,165,388 | 11/1992 | Hartinger | 128/24 EL |
| 5,195,509 | 3/1993 | Rentschler et al. | 128/24 EL |

FOREIGN PATENT DOCUMENTS 0483396 10/1990 European Pat. Off. .

*Primary Examiner*—Lee S. Cohen

*Assistant Examiner*—Krista M. Pfaffle

*Attorney, Agent, or Firm*—Hill, Steadman & Simpson

[57] ABSTRACT

An acoustic wave generator has a shockwave source contained in a housing with a volume between the shockwave source and the location at which the acoustic waves exit the generator which is divided into two sub-volumes, each filled with acoustic propagation medium. The location at which the acoustic waves exit the generator is in the form of a deformable cushion which permits the generator to conform to the surface of a subject to be irradiated with the acoustic waves. The liquid propagation medium in both sub-volumes is circulatable, with the amount of liquid propagation medium in the sub-volume forming the cushion being variable.

8 Claims, 2 Drawing Sheets

ACOUSTIC WAVE GENERATOR HAVING A CIRCULATABLE, LIQUID ACOUSTIC PROPAGATION MEDIUM

BACKGROUND OF THE INVENTION

1. Field of the Invention

The present invention is directed to an acoustic wave generator of the type having a deformable application cushion and an acoustic wave source within a housing, defining a volume therebetween filled with acoustic propagation medium.

2. Description of the Prior Art and Related Application

A pressure pulse generator is disclosed in co-pending U.S. application Ser. No. 07/761,392, now U.S. Pat. No. 5,207,215, filed Sep. 18, 1991, (Rattner et al), assigned to the same Assignee (Siemens AG) as the present application, wherein the volume containing the acoustic propagation medium, defined between a flexible bellows forming an application cushion and the shockwave source is divided by a wall into two sub-volumes. A first of these sub-volumes is situated between the wall and the pressure pulse source, and is in fluid communication with a reservoir for the liquid acoustic propagation medium via two main lines, so that the acoustic propagation medium contained in the first sub-volume can be circulated.

Pressure pulse generators of this type are used, for example, in medicine for the purpose of treating stone pathologies (lithotripsy), for treating tumors and for treating bone pathologies (osteorestoration). Such pressure pulse sources can also be used for non-medical purpose. The pressure pulse source within the pressure pulse generator can be of the type used to generate shockwaves, or may be of the type to generate diagnostic ultrasound, for example for ultrasound imaging, or for generating therapeutic ultrasound, for example, for treating hyperthermia. The pressure pulse generator may also be suit for generating pressure pulses for materials testing or other purposes. In any case, the generator is acoustically coupled to the subject to be charged with acoustic waves by means of an application cushion, and the subject and the generator are aligned relative to each other so that the acoustic waves pass through the region of the subject which is intended to be acoustically irradiated.

In pressure pulse generators of this type, the separation of the space between the pressure pulse source and the application cushion into two sub-volumes permits the quantity of acoustic propagation medium contained in the second sub-volume, situated between the application cushion and the dividing wall, to be varied for the purpose of acoustically coupling and uncoupling the generator to or from the subject. Upon delivery of acoustic propagation medium to the second sub-volume, the application cushion is forced against the surface of the subject under the influence of the liquid pressure. When the acoustic propagation medium is removed from the second sub-volume, the application cushion falls away from the surface of the subject. Independently thereof, the acoustic propagation medium in the first sub-volume can, for example, be circulated through a cooling system for the purpose of cooling the pressure pulse source, and can be brought to a pressure which can assist in the operation of the source for generating acoustic waves, for example, to influence the movement of the electrically conductive membrane relative to the coil if an electrodynamic pressure pulse source is used. A reservoir and a fluid circulator are required both for the acoustic propagation medium contained in the first sub-volume and in the second sub-volume. This requires known pressure pulse generators of this type to be constructed in a relative complicated manner, and such devices are correspondingly expensive. Moreover, this known type of generator occupies a relatively large space.

SUMMARY OF THE INVENTION

It is an object of the present invention to provide an acoustic wave generator of the type having a volume filled with acoustic propagation medium which is divided into two sub-volumes, through which the liquid acoustic propagation medium can be circulated, which is simple and economic in construction and which occupies as small a space as possible.

The above object is achieved in accordance with the principles of the present invention in an acoustic wave generator including an acoustic wave source and an application cushion defining a volume containing acoustic propagation medium, with a liquid-tight wall disposed between the source and the cushion which subdivides the volume into two sub-volumes filled with liquid acoustic propagation medium, and having a reservoir for the acoustic propagation medium in fluid communication via two main lines with the first sub-volume. The first sub-volume is adjacent the acoustic wave source and the second sub-volume is adjacent the application cushion. Fluid conveying means for circulating the acoustic propagation medium between the reservoir and the first sub-volume via the two main lines are provided. A branch line connectable to one of the main lines and is in fluid communication with the second sub-volume. Valve means are provided for connecting the one main line to the branch line leading to the second sub-volume while simultaneously connecting the two main lines and separating the other main line from the reservoir, thereby permitting the quantity of acoustic propagation medium contained in the second sub-volume to be varied by the fluid circulator (fluid conveying means). Both the reservoir and fluid circulator are connectable to both sub-volumes, so that the structure of the generator is much simpler and more economic and requires less installation space that conventional generators of this type.

Another advantage of the invention is that the relatively large cross-sections of both main lines are available when varying the quantity of acoustic propagation medium contained in the second sub-volume, so that the fluid handling capacity of the fluid conveyor can be increased for accelerating the coupling or uncoupling procedure. Because at least a partial exchange of acoustic propagation medium between the first and second sub-volumes will occur when varying the quantity of acoustic propagation medium contained in the second sub-volume, measures which can be employed to degasify and/or clean, such as by filtering, the acoustic propagation medium primarily for reasons associated with the acoustic propagation medium in the first sub-volume will also be effective for the acoustic propagation medium contained in the second sub-volume.

Preferably, the valve means is formed by first and second valves, with the line discharging into the second sub-volume being connectable to one main line via the first valve, and a connection of the main lines to each other being produced with the second valve, which also separates the other main line from the reservoir.

In a preferred embodiment of the invention, the acoustic wave source, the application cushion, the wall and the two sub-volumes filled with the acoustic propagation medium, as well as the line discharging into the second sub-volume and the first valve are contained in an application assembly which is connected via the two main lines to a supply assembly, which contains the reservoir, the fluid circulator, and the second valve. In comparison to known generators, therefore, only two lines for the acoustic propagation medium are required for connecting the supply assembly and the application assembly.

In a further embodiment of the invention, the circulation direction of the fluid circulator is reversible. The circulation of the acoustic propagation medium contained in the first sub-volume, or an increase in the quantity of acoustic propagation medium contained in the second sub-volume, can then optionally be undertaken by operating the fluid circulator in a first direction. Reducing the quantity of acoustic propagation medium contained in the second sub-volume is then undertaken by operating the fluid circulator in the opposite direction. If, alternatively, the fluid circulator has a fixed (unchangeable) circulation direction, the delivery side of the fluid circulator is optionally connectable to the one main line, or to the reservoir, via a third valve. Simultaneously with the connection of this main line to the delivery side of the fluid circulator, the inlet side of the fluid circulator is connected to the supply reservoir. Given connection of the supply reservoir to the delivery side of the fluid circulator, the inlet side of the fluid circulator is connected to one main line and the reservoir is separated from the inlet side of the fluid circulator.

In a preferred embodiment of the invention if the acoustic wave source is of the type having a membrane which can be driven impact-like, an elevated static pressure, in comparison to the ambient pressure, can be maintained in the first sub-volume while circulating the acoustic propagation medium to assist in returning the membrane to its initial position after displacement of the membrane.

As used herein, the term "valve means" will be understood to encompass an individual valve as well as the combination of a plurality of valves.

DESCRIPTION OF THE PREFERRED EMBODIMENTS

Figure 1:
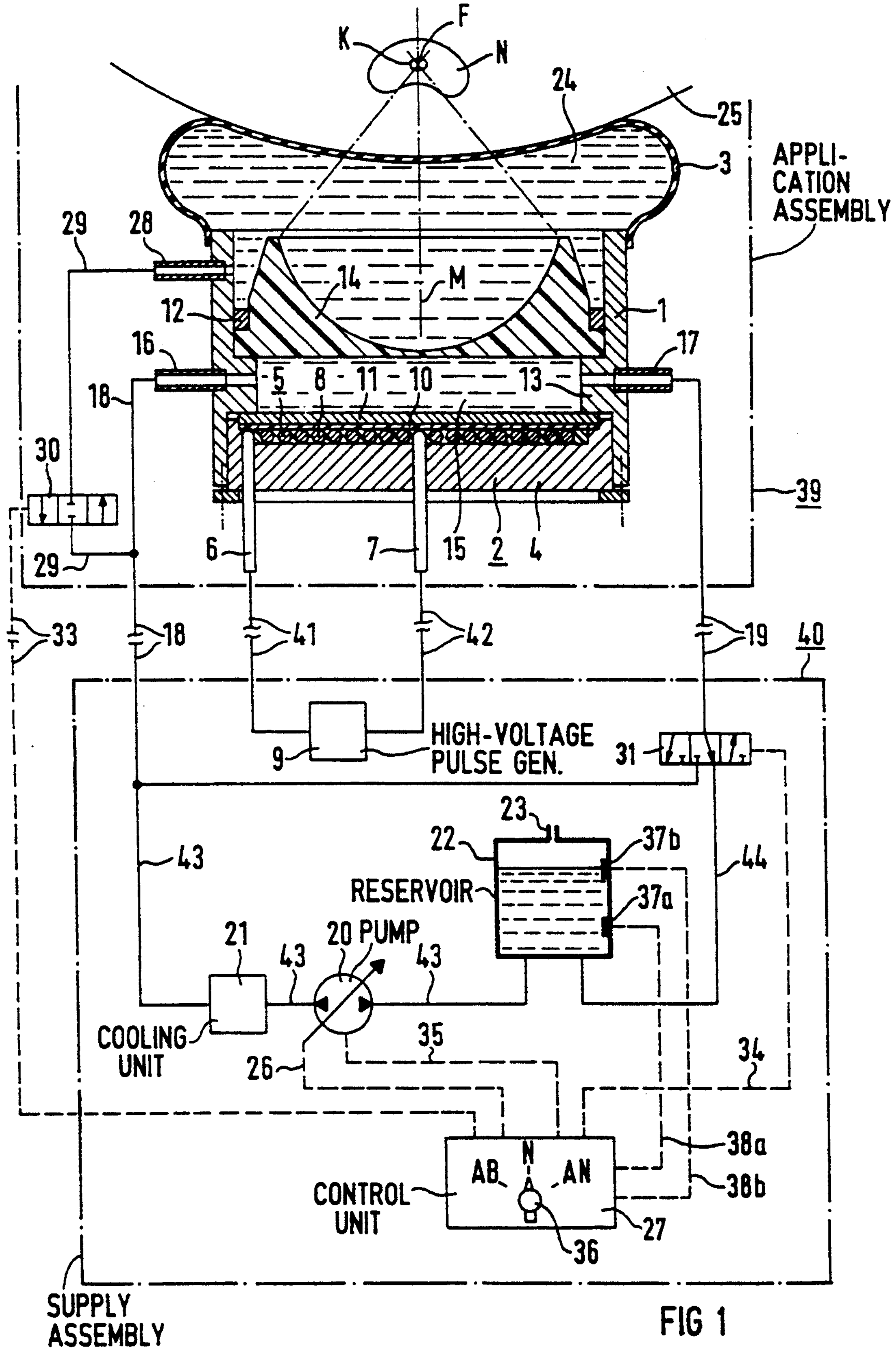
FIG. 1 is a schematic diagram of a first embodiment of an acoustic wave generator constructed in accordance with the principles of the present invention, having a reversible circulation direction.

A first embodiment of an acoustic wave generator is shown in FIG. 1 in the form of a pressure pulse generator of the type for generating shockwaves for disintegrating calculi in vivo in a patient. As a source of acoustic waves, the generator has a pressure pulse source, namely a shockwave source, generally referenced 2, which is disposed at, and closes, one end of a tubular housing 1. The opposite end of the housing 1 is closed by a flexible application membrane 3.

The shockwave source 2 has a coil 5 arranged on a planar seating surface of a coil carrier 4. The coil 5 has a plurality of spiral turns, one of which is reference 8, disposed between an electrically connecting terminals 6 and 7. The coil carrier 4 is formed of an electrically insulating material, for example, aluminum oxide ceramic. The space between the turns 8 of the coil 5 is filled with an electrically insulating casting resin. The terminals 6 and 7 of the coil 5 are connected to an electrical high-voltage pulse generator 9. The side of the coil carrier 5 facing away from the coil carrier 4 is covered by a disc-shaped, planar membrane 11, with an insulating foil 10 being disposed between the coil 5 and the planar membrane 11. The planar membrane 11 consists of flexible electrically conductive material, for example aluminum. The membrane 11, the insulating foil 10 and the coil 5 are combined with the coil carrier 4 to form a unit, with the components being centered within the unit. This unit is pressed against a shoulder 13 provided in an opening in the housing 1 by means of a ring adjacent to the coil carrier 4 and several screws, only the center lines of two screws being schematically indicated with dot-dash lines. The membrane 11 is thereby pressed liquid-tight against the shoulder 13.

A plano-concave acoustic positive lens 14 composed, for example, of polystyrol, has a planar side pressed liquid-tight against a side of the shoulder 13 facing away from the membrane 11. The positive lens 14 is axially fixed by a schematically indicated retaining ring 12 introduced into the bore opening of the housing 1. A first sub-volume 15 which contains a liquid acoustic propagation medium, for example water, is situated between the positive lens 14 and the membrane 11. The first sub-volume 15 has two ports 16 and 17, respectively connected to main lines or conduits 18 and 19. (In the drawings, solid lines indicate fluid lines and dashed lines indicate electrical lines.) Both main lines 18 and 19 are in fluid communication with a reservoir 22, which simultaneously serves as a bubble separator, and which can be charged with an under-pressure (i.e., a pressure less than ambient pressure) via a stem 23 for degasification of the water, if necessary. The water can be circulated with a pump 20 connected in a line 43 which connects the main line 18 to the reservoir 22. The water thereby flows through a schematically-indicated cooling unit 21 connected in the line 43.

The same liquid contained in the first sub-volume 15 is also contained in a second sub-volume 24 situated between the positive lens 14 and the application membrane 3. The second sub-volume 24 is separated liquid-tight from the first sub-volume 15 by the positive lens 14, which forms a wall therebetween.

For conducting a treatment, the shockwave generator is pressed against the body of a patient 25 to be treated by means of the flexible membrane 3. Shockwaves are generated in a known manner by charging the coil 5 with a high-voltage pulse from the high-voltage pulse generator 9. In response thereto, the coil 5 generates a magnetic field extremely rapidly. This causes a current flow in the membrane 11 in a direction opposite to the direction of current flow through the coil 5. The current in the membrane 11 also has an associated magnetic field which is oppositely directed to the magnetic field associated with the current flowing through the coil 5. As a consequence of the repelling forces thereby arising, the membrane 11 is rapidly moved away from the coil 5, causing a pressure pulse, which is initially planar, to be introduced into the water contained in the first sub-volume 15 and adjacent to the membrane 11, functioning as the acoustic propagation medium. This pressure pulse is focused by the positive lens 14 onto a focal zone F in the manner indicated by the dot-dash lines in FIG. 1. The focal zone F lies on the center axis M of the shockwave generator. The focused pressure pulse propagates in the water contained in the second sub-volume 24, also functioning as an acoustic propagation medium. The shockwave generator is oriented with respect to the patient 25 by means of a known locating system, for example, an x-ray locating system, so that a calculus K to be disintegrated, for example, a stone of a kidney N, is situated in the focal zone F. The calculus K can then be disintegrated by a series of pressure pulses, which have steepened into shockwaves, so that the stone is fragmented into grains so small as to be able to be eliminated naturally. The pressure pulses emanating from the membrane 11 gradually intensify into the shockwaves during their passage through the water contained in the first and second sub-volumes 15 and 24, as well as during their passage through the body tissue of the patient 25. A shockwave is a pressure pulse having an extremely steep leading front.

The schematically indicated pump 20 in the embodiment of FIG. 1 is a pump having variable throughput capacity. The throughput capacity of the pump 20 is set by a schematically indicated control unit 27 via a control line 26. The throughput capacity of the pump 20 is set during normal operation so that the water situated in the first sub-volume 15 is maintained at a static overpressure of, for example, approximately 1 bar in comparison to the ambient pressure. As a result, the membrane 11, whose thickness is shown exaggerated in FIG. 1, is returned to its initial position after each generation of a pressure pulse (shockwave) so as to be forced flush against the surface of the coil 5 (with the insulating foil 10 interposed therebetween) in a defined initial position. This assures that successively generated pressure pulses (shockwaves) will each have the same acoustic characteristics.

As further shown in FIG. 1, the second sub-volume 24 has a port 28, which discharges into the second sub-volume 24, and which is connected via a branch line 29 having a valve 30 to the main line 18. The valve 30 has three positions among which it can be switched. In the middle position, which corresponds to normal operation of the shockwave generator, the line 29 is interrupted, so that water situated in the first sub-volume 15 circulates through the cooling unit 21. The valve 30 is constructed so that neither water from the second sub-volume 24 nor from the main line 18 can emerge through those sections of the line 29 which are disconnected by the valve 30 in this middle position.

When the valve 30 is switched to a position to connect its right-most portion in the line 29, the valve 30 is transmissive to enable delivery of water into the second sub-volume 24. Conversely, when the valve 30 is switched to bring its left-most portion into the line 29, the valve 30 is transmissive to enable removal of water from the second sub-volume 24.

The main line 19 leads to a further valve 31 which also has three switchable positions. In the middle position, corresponding to normal operation of the shockwave generator, the valve 31 produces a connection of the main line 13 to the reservoir 22. In both its left-most and right-most positions, the valve 31 produces a connection between the main line 19 and a line 32, which is connected to the main line 18 at a junction disposed between the pump 20 and the port 16. The valve 31 is constructed so that the line 32 is closed liquid-tight in the middle position, and so that the line 44 leading from the reservoir 22 to the valve 31 is closed liquid-tight in the two other switch positions. The valves 30 and 31 are connected to the control unit 27 via respective control lines 32 and 34.

A further control line 35 connects the control unit 27 to the pump 20. The pump 20, as indicated, is a pump having a reversible throughput direction, and the control unit 27 can switch the throughput direction of the pump 20 via the control line 35.

The control unit 27 has a switch 36 with which three different operating conditions of the shockwave generator of the invention can be set. In the middle switch position, referenced N, for the switch 36, the shockwave generator is in the aforementioned, normal operation mode, in which the water in the first sub-volume 15 is circulated through the cooling unit 21 and through the bubble separator/reservoir 22 by means of the pump 20. In this normal mode, the control unit 27 respectively actuates the valves 30 and 31 so that they are in their middle switch positions. The throughput direction of the pump 20 is set by the control unit 27 so that the water is circulated from the reservoir 22 through the cooling unit 21 into the first sub-volume 15 and back into the reservoir 22. The throughput capacity of the pump 20 is also set by the control unit 27 so that, as described, a pressure sufficient for restoring the membrane 11 to its initial position is maintained in the first sub-volume 15.

The two other switch positions of the switch 36 serve the purpose of varying the quantity of water (acoustic propagation medium) situated in the second sub-volume 24, for coupling and uncoupling the shockwave generator to or from the body of the patient 25. Coupling ensues by turning the switch 36 to the switch position AN, causing both of the valves 30 and 31 to be positioned so that their right-most portions are connected in the respective lines. This causes water to be introduced into the second sub-volume 24, so that the application membrane 3 is pressed against the body surface of the patient 25 under the pressure of the water.

Uncoupling ensues with the switch 36 in the position referenced AB, which causes the respective left-most portions of the valves 30 and 31 to be connected in the respective lines. This causes a sufficient amount of water to be removed from the second sub-volume 24 so that the application membrane 3 lies only loosely against the body surface of the patient 25, or is completely separated therefrom.

When the switch 36 is in the position AN, the throughput direction of the pump 20 is the same as in the middle, normal position, i.e., the same as during normal operation of the shockwave generator. Turning the switch 36 to the position AB causes the pump 20 to operate with an opposite throughput direction, i.e., the pump 20 conveys water into the reservoir 22. Thus during both application (switch position AN) and during deapplication (switch position AB) of the shockware generator, the connecting branch 28 discharging into the second sub-volume 25 is connected to the main line 18 via the line 29 with the valve 30, and simultaneously the main line 19 is separated from the reservoir 22 by the valve 31 and is connected to the main line 18.

Water is then conveyed from the reservoir 22 into the second sub-volume 24 (application), or water is returned from the second sub-volume 24 into the reservoir (de-application).

Because the sum of the cross sections of the two main lines 18 and 19 is available as a total line cross section during application and de-application, as a consequence of the connection which exists between the main lines 18 and 19 via the line 32, the control unit 27 switches the pump 20 to an increased throughput capacity during application or de-application. It is preferable, therefore, to provide the line 29 and the line 23 (which lies between the reservoir 22 and the junction of the line 32 with the main line 18) with individual cross sections so that a sum of those cross sections at least corresponds to the sum of the cross sections of the main lines 18 and 19. The cross section of the line 32 is preferably selected at least equal to the cross section of the main line 19. The flow cross sections of the valves 30 and 31 are selected so that these valves do not represent throttle locations in any of the operating modes.

The shockwave source 2 with the housing 1, the coupling membrane 3 and the positive lens 14 separating the two sub-volumes 15 and 24, is combined with the valve 30 and the line 29 to form an application assembly 39, as indicated by the dot-dash lines in FIG. 1. The high-voltage pulse generator 9, the pump 20, the cooling unit 21, the reservoir 22, the control unit 27 and the valve 31 with the line 32 are combined to form a supply assembly 40, as also indicated by dot-dash lines in FIG. 1. The application assembly 39 is connected to the supply assembly 40 only by the two main lines 18 and 19, the control line 33, and the high-voltage lines 41 and 42 which connect the terminals 6 and 7 to the high-voltage pulse generator 9. All of these lines are shown schematically shortened in FIG. 1.

Figure 2:
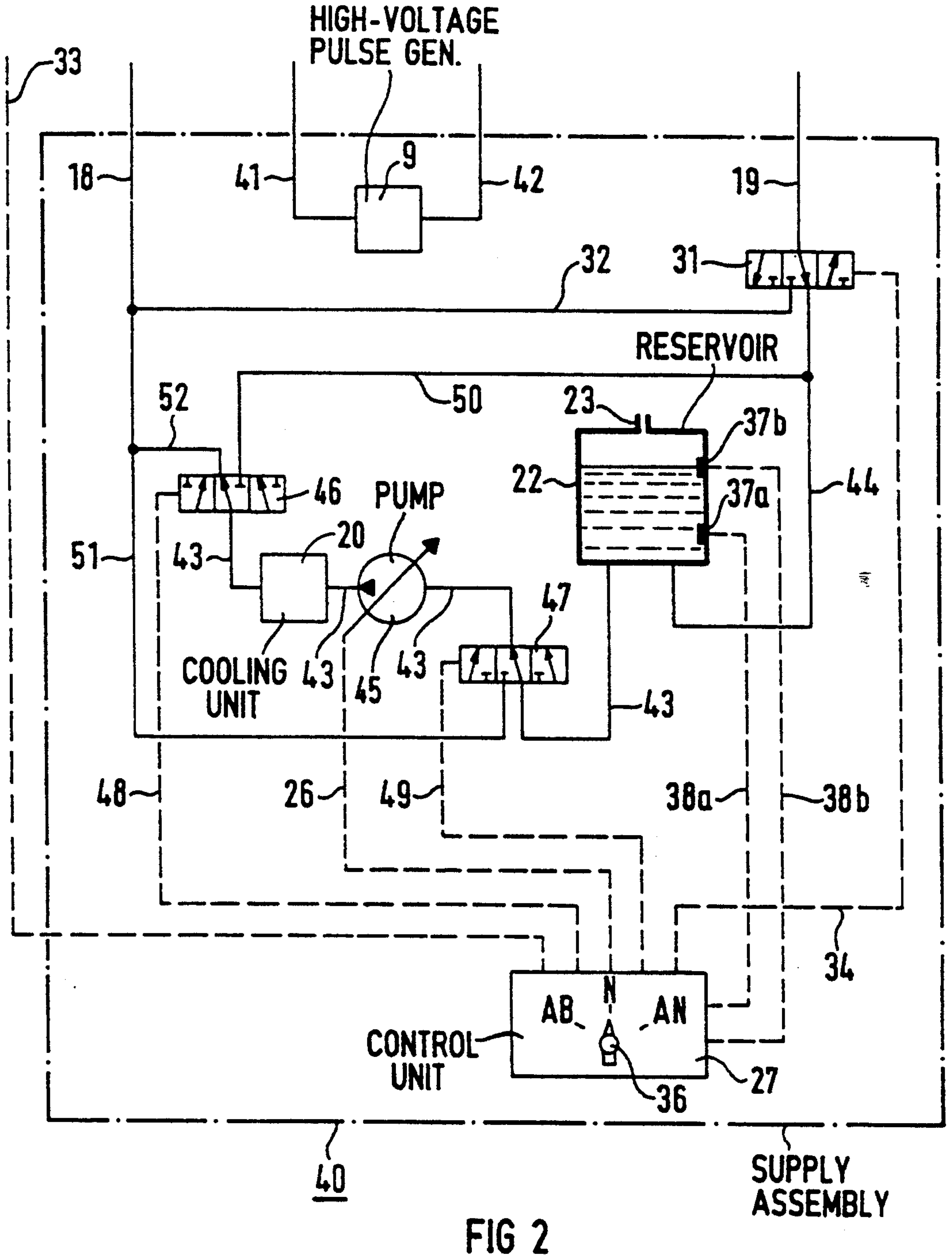
FIG. 2 is a block diagram of a portion of a further embodiment of an acoustic wave generator constructed in accordance with the principles of the present invention, having a fluid circulator with a fixed circulation direction.

The embodiment of the shockwave generator shown in FIG. 2 differs from the embodiment of FIG. 1 only with respect to the supply assembly 40, the embodiment of FIG. 2 having a pump 45 with a fixed throughput direction. In order to be able nonetheless to optionally supply water to, or remove water from, the second sub-volume 24 as needed, two further valves 46 and 46 are provided which are actuated by the control unit 27 via respective control lines 48 and 49. The valves 46 and 47 also each have three switch positions which they assume dependent on the position of the switch 36, the middle position for valves 46 and 47 corresponding to normal operation in the application mode (position AN of the switch 36), the valves 46 and 47 will be switched so that their respective right-most portions are connected in the respective lines. In the de-application mode (position AB of the switch 36), the respective left-most portions of the valves 46 and 47 will be connected in the respective lines.

Three additional lines 50, 51 and 52 are also present in the embodiment of FIG. 2. Via the valve 46 and the line 52, the delivery side of the pump 45 can be connected optionally to the main line 18 or to the reservoir 22 via the line 50 discharging into the line 44. Upon connection of the main line 18 to the delivery side of the pump 45, the inlet side of the pump 45 is simultaneously connected to the reservoir 22 by the valve 47. Given connection of the reservoir 22 to the delivery side of the pump 45, the inlet side of the pump 45 is connected to the main line 18 via the valve 47 and the line 43 and the line 51, into which the line 52 discharges. Additionally, the reservoir 22 is separated from the inlet side of the pump 45. During normal operation and during the application mode, the delivery side of the pump 45 is connected to the main line 18, and during the de-application mode the inlet side of the pump 45 is connected to the main line 18. Thus all three operating modes can achieved using a pump having a fixed throughput direction.

In order to limit the amount of water deliverable to the sub-volume 24, or removable therefrom, two level sensors 37*a* and 37*b* are disposed in the reservoir 22. The level sensors 37*a* and 37*b* are connected to the control unit 27 via respective signal lines 38*a* and 38*b*. When the control unit 27 is switched to the application by means of the switch 36 for such a long time that the water level in the reservoir 22 drops to the level of sensor 37*a*, the sensor 37*a* forwards a corresponding signal via the signal line 38*a* to the control unit 27, which terminates the application procedure in response thereto. Conversely, the control unit 27 terminates the de-application procedure when the water level in the reservoir 22 reaches the level of the sensor 37*b*, which thereupon forwards a corresponding signal to the control unit via the signal line 38*b*. The level sensors 37*a* and 37*b* may be float-type switches.

For measuring the liquid pressure in the second sub-volume 24, a pressure sensor can be provided in a known manner, the output signal thereof being supplied to the control unit 27, which can terminate the application procedure and switch to a normal operation mode when a defined pressure is reached.

The invention has been described above with reference to the example of a shockwave generator having an electromagnetic shockwave source. The invention can, however, also be employed shockwave generators or pressure pulse generators having shockwave sources or pressure pulse sources which function differently, for example piezoelectrically. The exemplary embodiment is a generator for non-evasive disintegration of calculi, however, the invention can be used in generators designed for other desired medical purposes, as well as for non-medical purposes. It is also possible to employ the invention in generators for other types of acoustic waves, for example ultrasound generators, which can be used for therapeutic, diagnostic or other purposes.

Although modifications and changes may be suggested by those skilled in the art, it is the intention of the inventor to embody within the patent warranted hereon all changes and modifications as reasonably and properly come within the scope of his contribution to the art.

I claim as my invention:

1. An acoustic wave generator comprising:

a housing having an application cushion disposed at one end and an acoustic wave source disposed at an opposite end with a volume therebetween containing a liquid acoustic propagation medium;

a liquid-tight wall in said housing dividing said volume into a first sub-volume adjacent said acoustic wave source and a second sub-volume adjacent said application cushion;

a reservoir for said liquid acoustic propagation medium connected to said first sub-volume by two main fluid lines;

fluid conveying means for circulating said liquid acoustic propagation medium through said first sub-volume and said reservoir via said two main lines;

a branch fluid line in fluid communication with said second sub-volume and connectable to one of said main lines; and valve means for simultaneously placing said branch line and said one of said main lines in fluid communication while also placing said two main lines in fluid communication and while also separating the other of said main lines from said reservoir, and for varying the quantity of said liquid acoustic propagation medium in said second sub-volume with said fluid conveying means.

2. An acoustic wave generator as claimed in claim 1 wherein said fluid conveying means has a throughput capacity, and includes means for increasing said throughput capacity when varying the quantity of said liquid acoustic propagation medium in said second sub-volume.

3. An acoustic wave generator as claimed in claim 1 wherein said valve means comprises:

a first valve connected between said one of said main lines and said branch fluid line for placing said branch line and said one of said main lines in fluid communication; and a second valve connected between said two main fluid lines and between said other of said main fluid lines and said reservoir for simultaneously placing said two main lines in fluid communication with each other and for separating said other of said main lines from said reservoir.

4. An acoustic wave generator as claimed in claim 3 wherein said housing, including said application cushion, said acoustic wave source, said wall, and said first and second sub-volumes comprise an application assembly together with said branch fluid line and said first valve, and wherein said reservoir, said fluid conveying means and said second valve comprise a supply assembly, said application assembly and said supply assembly being in fluid communication only via said two main lines.

5. An acoustic wave generator as claimed in claim 1 wherein said fluid conveying means has a reversible throughput direction, and further comprising means for operating said fluid conveying means in a first throughput direction for increasing the quantity of said liquid acoustic propagation medium in said second sub-volume and for operating said fluid conveying means in a second throughput direction, opposite to said first throughput direction, for decreasing the quantity of said liquid acoustic propagation medium in said second sub-volume.

6. An acoustic wave generator as claimed in claim 1 wherein said fluid conveying means has a fixed throughput direction and has a delivery side and an inlet side, and wherein said acoustic wave generator further comprises further valve means for optionally placing said delivery side of said fluid conveying means in fluid communication with said one main line or in fluid communication with said reservoir and for simultaneously placing said inlet side of said fluid conveying means in fluid communication with said reservoir if said delivery side of said fluid conveying means is in fluid communication with said one main line and for simultaneously placing said inlet side of said fluid conveying means in fluid communication with said one main line and disconnecting said reservoir from said inlet side of said fluid conveying means if said delivery side of said fluid conveying means is in fluid communication with said reservoir.

7. An acoustic wave generator as claimed in claim 6 wherein said valve means comprises:

a first valve connected between said one of said main lines and said branch fluid line for placing said branch line and said one of said main lines in fluid communication;

a second valve connected between said two main fluid lines and between said other of said main fluid lines and said reservoir for simultaneously placing said two main lines in fluid communication with each other and for separating said other of said main lines from said reservoir; and wherein said housing, including said application cushion, said acoustic wave source, said liquid-tight wall and said first and second sub-volumes comprise an application assembly together with said branch fluid line and said first valve and wherein said reservoir, said second valve, said further valve means and said fluid conveying means comprise a supply assembly, said application assembly and said supply assembly being in fluid communication only via said two main lines.

8. An acoustic wave generator as claimed in claim 1 wherein said acoustic wave source comprises:

a flexible membrane disposed for interacting with said liquid acoustic propagation medium in said first sub-volume;

means for driving said membrane to provide an impact to said membrane for rapidly displacing said membrane from an initial position into said liquid acoustic propagation medium in said first sub-volume; and wherein said fluid conveying means forms means for maintaining a static pressure in said first sub-volume, which is elevated in comparison to ambient pressure, when circulating said liquid acoustic propagation medium through said first sub-volume for returning said membrane to said initial position after displacement of said membrane.

* * * * *